(12) United States Patent
Yoneto (10) Patent No.: US 10,842,741 B2
(45) Date of Patent: Nov. 24, 2020

(54) ORAL MUCOSA APPLICATION MATERIAL AND METHOD FOR PRODUCING SAME THEREFOR

(71) Applicant: RITAPHARMA, CO., LTD., Kyoto (JP)

(72) Inventor: Kunio Yoneto, Kyoto (JP)

(73) Assignee: RITAPHARMA, CO., LTD., Kyoto (JP)

( * ) Notice: Subject to any disclaimer, the term of this patent is extended or adjusted under 35 U.S.C. 154(b) by 0 days.

(21) Appl. No.: 16/320,017

(22) PCT Filed: Jul. 25, 2017

(86) PCT No.: PCT/JP2017/026898
§ 371 (c)(1),
(2) Date: Jan. 23, 2019

(87) PCT Pub. No.: WO2018/021326
PCT Pub. Date: Feb. 1, 2018

(65) Prior Publication Data
US 2019/0262259 A1    Aug. 29, 2019

(30) Foreign Application Priority Data
Jul. 27, 2016  (JP) .................. 2016-147076

(51) Int. Cl.
| | | |
|---|---|---|
| *A61K 9/00* | (2006.01) | |
| *A61K 9/70* | (2006.01) | |
| *A61K 47/36* | (2006.01) | |
| *A61K 8/02* | (2006.01) | |
| *A61K 47/38* | (2006.01) | |

(52) U.S. Cl.
CPC ............ *A61K 9/006* (2013.01); *A61K 9/0056* (2013.01); *A61K 9/70* (2013.01); *A61K 47/36* (2013.01); *A61K 8/0208* (2013.01); *A61K 47/38* (2013.01)

(58) Field of Classification Search
CPC .......... A61K 9/006; A61K 9/70; A61K 47/36; A61K 9/0056; A61K 8/0208; A61K 47/38; A61K 47/10; A61K 47/26; A61P 1/02
See application file for complete search history.

(56) References Cited

U.S. PATENT DOCUMENTS

| | | |
|---|---|---|
| 2001/0041166 A1 | 11/2001 | Saito et al. |
| 2009/0325861 A1 | 12/2009 | Goodheart |
| 2011/0274756 A1 | 11/2011 | Geistlich et al. |

FOREIGN PATENT DOCUMENTS

| | | |
|---|---|---|
| CN | 104984390 A | 10/2015 |
| JP | 54-41320 A | 4/1979 |
| JP | 2000-256189 A | 9/2000 |
| JP | 2000-319167 A | 11/2000 |
| JP | 2001-163745 A | 6/2001 |
| JP | 2005-263759 A | 9/2005 |
| JP | 2008-295885 A | 12/2008 |
| JP | 2012-515035 A | 7/2012 |
| KR | 100885178 B1 | 2/2009 |
| WO | 02/09637 A2 | 2/2002 |
| WO | 2008/027904 A2 | 3/2008 |
| WO | 2010/013656 A1 | 2/2010 |
| WO | 2010/083487 A1 | 7/2010 |
| WO | 2013/139955 A1 | 9/2013 |

OTHER PUBLICATIONS

Extended (Supplementary) European Search Report dated Feb. 21, 2020, issued in counterpart EP Application No. 17834328.1. (9 pages).
International Search Report dated Oct. 17, 2017, issued in counterpart International Application No. PCT/JP2017/026898 (2 pages).

*Primary Examiner* — Snigdha Maewall
(74) *Attorney, Agent, or Firm* — Westerman, Hattori, Daniels & Adrian, LLP (57) ABSTRACT

Provided is a novel oral mucosa application material that has good handling properties, has excellent application properties for being applied to the oral mucosa even if moisture or saliva on the surface of the oral mucosa is heavy, and is provided with a property for improving the effect of physically protecting an application site by containing the moisture or saliva after application and showing elasticity, and further, a property for remaining at the application site for a long time. This oral mucosa application material is provided with a freeze-dried body containing a polymer on an adhesion surface to the oral mucosa. The content of the polymer in the freeze-dried body is 20 mass % or more, and the content of hyaluronic acid in the polymer is 50 mass % or more.

13 Claims, 1 Drawing Sheet

ORAL MUCOSA APPLICATION MATERIAL AND METHOD FOR PRODUCING SAME THEREFOR

TECHNICAL FIELD

The present invention relates to an oral mucosa patch and a method for producing the oral mucosa patch.

BACKGROUND ART

Areas other than teeth in an oral cavity are covered with a kind of mucosa called oral mucosa. Various diseases occur in the oral mucosa, and these diseases are collectively referred to as oral mucosal diseases or the like.

As oral mucosal diseases, aphthous stomatitis (so-called stomatitis), catarrhal stomatitis, ulcerative stomatitis and the like of which the symptoms are widely developed even in healthy persons are also known.

For example, the aphthous stomatitis generates grayish white spots with a diameter of about several millimeters on the oral mucosa and is accompanied by pain, and once the stomatitis gets worse, blood oozes from the grayish white spots. Eating may be accompanied by extreme pain due to food stimulation, and in a severe case, it may be impossible to eat.

Among oral mucosal diseases, oral mucositis is supposed to be the most frequent side effect of side effects occurring in mouth of patients receiving anticancer drug treatment and radiation treatment. For example, anticancer drug treatment causes inflammation on mucosa inside a cheek and a lip and leads to symptoms such as mucosal abrasion in some cases. Once the symptom becomes severe, it is almost impossible to take the meal by mouth due to pain or the like, and necessity for discontinuing the anticancer drug treatment may arise.

On the other hand, film preparations, tablets and powders used for treating various diseases occurring in oral cavity by being stuck to the oral mucosa have been conventionally known (e.g. see Patent Documents 1 and 2).

PRIOR ART DOCUMENTS

Patent Documents

Patent Document 1: Japanese Patent Laid-open Publication No. 2001-163745
Patent Document 2: Japanese Patent Laid-open Publication No. 54-041320

SUMMARY OF THE INVENTION

Problems to be Solved by the Invention

As described above, film preparations, tablets and powder preparations used so as to be stuck to the oral mucosa have been known, but these conventional film preparations, tablets and the like have insufficient stickability when there is a lot of moisture on the oral mucosa surface. For example, Precautions for Use in a package insert of a commercial product AFTACH® oral patch (tablet) describes "When the affected mucosa is remarkably wet with saliva, the patch may not adhere, and so please stick the patch after lightly wiping off the saliva by tissue paper, gauze or the like beforehand". In addition, for example, Dosage Regimen in a package insert of a commercial stomatitis patch TAISHO QUICK CARE (film preparation) describes "Please lightly wipe off moisture/saliva or the like on an affected part after cleansing the affected part by gargle or the like". In addition, for example, there is a problem that, depending on the moisture amount in the oral cavity, a film preparation or the like is readily peeled off from the mucosa when eating and drinking in a state that the film preparation or the like is stuck on the oral mucosa. For example, some film preparations containing water-soluble polymers dissolve in saliva in the oral cavity in a short time. In addition, since tablets are poor in flexibility, the tablets are unsuitable for use on a wide range of sites such as tongue surface and sublingual site which are soft and movable. In addition, the powder preparation requires a dedicated jig for application on the mucosa and is not easy to use.

Under such circumstances, the main object of the present invention is to provide a novel oral mucosa patch which is good in handleability, and has an excellent stickability of sticking to the oral mucosa even when there is a lot of moisture and saliva on the oral mucosa surface, and has a property of enhancing the physical protective effect for the stuck site by impregnating moisture and saliva to exhibit elasticity after sticking, and further a property of remaining on the stuck site for a long period.

Means for Solving the Problem

The inventor of the present invention conducted intensive studies to solve the above problems. As a result, the inventor has found that an oral mucosa patch having a lyophilizate containing a polymer on the adherend surface with the oral mucosa can be obtained, which contains 20 mass % or more of polymer in the lyophilizate and 50 mass % or more of hyaluronic acid in the polymer, thereby is good in handleability, and has the excellent stickability of sticking to the oral mucosa even when there is a lot of moisture and saliva on the oral mucosa surface, and has the property of enhancing the physical protective effect for the stuck site by impregnating moisture and saliva to exhibit elasticity after sticking, and further the property of remaining on the stuck site for a long period. On the basis of this finding, the present invention has been completed by further studies.

That is, the present invention provides the following aspects.

Item 1. An oral mucosa patch having a lyophilizate containing a polymer on an adherend surface with an oral mucosa, wherein
a polymer content in the lyophilizate is 20 mass % or more, and
a hyaluronic acid content in the polymer is 50 mass % or more.

Item 2. The oral mucosa patch according to Item 1, wherein the hyaluronic acid has a molecular weight of $1 \times 10^5$ daltons or more.

Item 3. The oral mucosa patch according to Item 1 or 2, wherein an intrinsic viscosity of the hyaluronic acid measured by the following measurement method is 3 dL/g or higher.
(Method for Measuring the Intrinsic Viscosity)

A solution prepared by measuring out 50 mg of hyaluronic acid and dissolving the hyaluronic acid in a 0.2 mol/L sodium chloride solution so that the total volume is 100 mL, and solutions prepared by measuring out 10 mL, 15 mL and 20 mL of this solution and adding a 0.2 mol/L sodium chloride solution to each of the solutions so that each total volume is 25 mL, are respectively used as sample solutions. For each sample solution and the 0.2 mol/L sodium chloride solution, specific viscosities are measured by the viscosity-measuring method in accordance with the standard of "General Tests, 2.53 Viscosity Determination, 1. Method I Viscosity measurement by capillary tube viscometer" in The 17th Edition of the Japanese Pharmacopoeia under an environment at 30.0±0.1° C. to calculate a reduced viscosity. A graph is made with the reduced viscosity on an ordinate and the hyaluronic acid concentration (g/100 mL) on an abscissa to determine the intrinsic viscosity from an intersection of a straight line connecting each point and the ordinate.

However, the specific viscosity and the reduced viscosity are determined from the following equations.

Specific viscosity=(Number of seconds for the sample solution to flow÷Number of seconds for 0.2 mol/L sodium chloride solution to flow)−1

Reduced viscosity=Specific viscosity÷Hyaluronic acid concentration (g/100 mL).

Item 4. The oral mucosa patch according to any one of Items 1 to 3, wherein the hyaluronic acid content in the lyophilizate is 0.1 mg/cm2 or more.
Item 5. The oral mucosa patch according to any one of Items 1 to 4, having:
  a base; and
  the lyophilizate laminated on the base.
Item 6. The oral mucosa patch according to any one of Items 1 to 5, wherein the lyophilizate contains 0 to 20 mass % of a polymer different from the hyaluronic acid.
Item. 7 The oral mucosa patch according to any one of Items 1 to 6, wherein the lyophilizate further contains an acid different from the hyaluronic acid.
Item 8. The oral mucosa patch according to any one of Items 1 to 7, wherein the lyophilizate further contains at least one of a sugar and a polyhydric alcohol.
Item 9. The oral mucosa patch according to any one of Items 1 to 8, which is used for preventing or treating an oral mucosal disease.
Item 10. The oral mucosa patch according to Item 9, wherein the oral mucosal disease is caused by cancer treatment.
Item 11. The oral mucosa patch according to any one of Items 1 to 8, which is used for hyposensitization therapy applied to the oral mucosa.
Item 12. The oral mucosa patch according to any one of Items 1 to 8, which is used for a transoral mucosally-absorbable preparation applied to the oral mucosa.
Item 13. A method for producing the oral mucosa patch according to any one of Items 1 to 12, including:
  preparing an aqueous solution containing a polymer;
  lyophilizing the aqueous solution,
wherein, as the polymer, a polymer containing 50 mass % or more of hyaluronic acid is used.

Advantages of the Invention

According to the aspect of the present invention, it is possible to provide an oral mucosa patch which is good in handleability, and has the excellent stickability of sticking to the oral mucosa even when there is a lot of moisture and saliva on the oral mucosa surface, and has the property of enhancing the physical protective effect for the stuck site by impregnating moisture and saliva to exhibit elasticity after sticking, and further the property of remaining on the stuck site for a long period. Since the oral mucosa patch according to the present invention exerts such excellent effects, the oral mucosa patch can be suitably used for preventing or treating oral mucosal diseases. Similarly, the oral mucosa patch according to the present invention can also be suitably used for hyposensitization therapy and a transoral mucosally-absorbable preparation applied to the oral mucosa. Furthermore, according to the aspect of the present invention, it is possible to provide a preferable method for producing the oral mucosa patch.

EMBODIMENTS OF THE INVENTION

The oral mucosa patch according to the present invention is an oral mucosa patch having a lyophilizate containing a polymer on the adherent surface with the oral mucosa, characterized in that a polymer content in the lyophilizate is 20 mass % or more and a hyaluronic acid content in the polymer is 50 mass % or more. Because of such a configuration, the oral mucosa patch according to the present invention is good in handleability, and has the excellent stickability of sticking to the oral mucosa even when there is a lot of moisture and saliva on the oral mucosa surface, and can exert the property of enhancing the physical protective effect for the stuck site by impregnating moisture and saliva to exhibit elasticity after sticking, and further the property of remaining on the stuck site for a long period. Thus, for example, the oral mucosa of a patient suffering from an oral mucosal disease can be suitably protected over a long period, and for example, pain accompanying eating and drinking can be reduced. Hereinafter, the oral mucosa patch and the method for producing the oral mucosa patch according the present invention will be described in detail.

The oral mucosa patch according to the present invention has a lyophilizate containing a polymer on the adherend surface with the oral mucosa. That is, in the oral mucosa patch according to the present invention, the lyophilizate serves as an adherend surface with the oral mucosa and is stuck to the surface of the oral mucosa for use. Note that the oral mucosa means areas other than teeth in the oral cavity, such as inside of cheek, upper jaw, tongue, sublingual site and gum.

The lyophilizate containing a polymer can be obtained e.g. by lyophilizing an aqueous solution containing a polymer. The lyophilizate has a shape of cotton, sponge or the like, and normally has a moisture content of 5 mass % or less.

In the oral mucosa patch according to the present invention, the polymer content in the lyophilizate is 20 mass % or more. Furthermore, the hyaluronic acid content in the polymer is 50 mass % or more. In the oral mucosa patch according to the present invention, since the adherend surface with the oral mucosa is composed of such a lyophilizate, handleability is good, stickability to the oral mucosa is excellent even when there is a lot of moisture and saliva on the oral mucosa surface, and the property of enhancing the physical protective effect for the stuck site by impregnating moisture and saliva to exhibit elasticity after sticking, and further the property of remaining on the stuck site for a long period can be provided.

That is, when the oral mucosa patch is applied to the oral cavity, the oral mucosa patch has sufficient shape retainability and is also difficult to adhere to hands and the like, and thus the oral mucosa patch is excellent in handleability. Furthermore, once the oral mucosa patch is stuck to the oral mucosa, the lyophilizate in the oral mucosa patch instantly absorbs moisture and saliva on the oral mucosa surface and adheres to the oral mucosa. In addition, after sticking to the oral mucosa, the oral mucosa patch impregnates moisture and saliva and forms a suitable elastic gelled matter to physically protect the stuck site. Furthermore, since this gelled matter is not thixotropic, damages and disintegrations due to physical movements of tongue and the like in the oral cavity are reduced, and a dissolution rate in moisture and saliva is slow, so that the oral mucosa patch remains at the stuck site for a long period. Consequently, the oral mucosa patch according to the present invention has the excellent stickability of sticking to the oral mucosa even when there is a lot of moisture and saliva on the oral mucosa surface, and suitably exerts the property of enhancing the physical protective effect for the stuck site by impregnating moisture and saliva to exhibit elasticity after sticking, and further the property of remaining on the stuck site for a long period.

In the present invention, the "hyaluronic acid" is used under a concept including hyaluronic acid and its salt. Thus, the "hyaluronic acid and its salt" is simply written as "hyaluronic acid" in some cases. The salt of the hyaluronic acid is not particularly limited, but examples thereof include sodium hyaluronate, potassium hyaluronate, magnesium hyaluronate, calcium hyaluronate and the like. In the present invention, each hyaluronic acid and its salt may be used alone or in combination of two or more kinds.

The average molecular weight of the hyaluronic acid is not particularly limited, but is preferably $1 \times 10^5$ daltons or higher, from the viewpoints that while the handleability of the oral mucosa patch is improved, the excellent stickability of sticking to the oral mucosa even when there is a lot of moisture and saliva on the oral mucosa surface, the property of enhancing the physical protective effect for the stuck site by impregnating moisture and saliva to exhibit elasticity after sticking, and further the property of remaining on the stuck site for a long period are exerted. Furthermore, the average molecular weight is preferably about $3.5 \times 10^5$ to $5 \times 10^6$ daltons, more preferably about $3.5 \times 10^5$ to $3 \times 10^6$ daltons, even more preferably about $6 \times 10^5$ to $2.3 \times 10^6$ daltons, particularly preferably about $1.2 \times 10^6$ to $2.3 \times 10^6$ daltons. As the hyaluronic acid, a hyaluronic acid having a single molecular weight, or mixed hyaluronic acids having a plurality of molecular weights may be used.

From the same viewpoint, the intrinsic viscosity of the hyaluronic acid measured by the following measurement method is not particularly limited, but is preferably 3 (dL/g) or higher. Furthermore, the intrinsic viscosity is preferably about 8 to 55 (dL/g), more preferably about 8 to 40 (dL/g), even more preferably about 10 to 40 (dL/g), particularly preferably about 15 to 40 (dL/g). As the hyaluronic acid, a hyaluronic acid having a single molecular weight, or mixed hyaluronic acids having a plurality of molecular weights may be used.

(Method for Measuring the Intrinsic Viscosity)

A solution prepared by measuring out 50 mg of hyaluronic acid and dissolving the hyaluronic acid in a 0.2 mol/L sodium chloride solution so that the total volume is 100 mL, and solutions prepared by measuring out 10 mL, 15 mL and 20 mL of this solution and adding a 0.2 mol/L sodium chloride solution to each of the solutions so that each total volume is 25 mL, are respectively used as sample solutions. For each sample solution and the 0.2 mol/L sodium chloride solution, specific viscosities are measured by the viscosity-measuring method in accordance with the standard of "General Tests, 2.53 Viscosity Determination, 1. Method I Viscosity measurement by capillary tube viscometer" in The 17th Edition of the Japanese Pharmacopoeia under an environment at 30.0±0.1° C. to calculate a reduced viscosity. A graph is made with the reduced viscosity on an ordinate and the hyaluronic acid concentration (g/100 mL) on an abscissa to determine the intrinsic viscosity from an intersection of a straight line connecting each point and the ordinate. Although the hyaluronic acid used as a raw material ordinarily contains a few percent of moisture, the "hyaluronic acid concentration" in the above equation means a concentration in terms of dry hyaluronic acid. However, the specific viscosity and the reduced viscosity are determined from the following equations.

Specific viscosity=(Number of seconds for the sample solution to flow÷Number of seconds for 0.2 mol/L sodium chloride solution to flow)−1

Reduced viscosity=Specific viscosity÷Hyaluronic acid concentration (g/100 mL).

The origin of the hyaluronic acid is not particularly limited, and e.g. a hyaluronic acid isolated and extracted from cock's comb, umbilical cord, etc., a hyaluronic acid prepared by fermentation using microorganisms such as *Streptococcus*, etc., or the like can be suitably used. In the present invention, as the hyaluronic acid, a commercial product can be used. As the hyaluronic acid, a hyaluronic acid which is not substantially chemically modified, or a chemically modified hyaluronic acid may be used.

Specific examples of the chemically modified hyaluronic acid include sodium carboxymethyl hyaluronate, hydroxypropyltrimonium hyaluronate, (C12-13) alkyl glyceryl hydrolyzed hyaluronate, propyleneglycol hyaluronate, acetylated sodium hyaluronate and the like. Each of the chemically modified hyaluronic acids may be used alone or in combination of two or more kinds.

In the oral mucosa patch according to the present invention, the hyaluronic acid content in the polymer contained in the lyophilizate is not particularly limited as long as the content is 50 mass % or more, but is preferably 60 mass % or more, more preferably 80 mass % or more. The hyaluronic acid content in the polymer may be substantially 100 mass %.

When a polymer other than hyaluronic acid (a polymer different from hyaluronic acid) is contained in the polymer contained in the lyophilizate, the content of the polymer is not particularly limited as long as the content is 50 mass % or less, but the content is preferably 40 mass % or less, more preferably 20 mass % or less from the viewpoints that while the handleability of the oral mucosa patch is improved, the excellent stickability of sticking to the oral mucosa even when there is a lot of moisture and saliva on the oral mucosa surface, the property of enhancing the physical protective effect for the stuck site by impregnating moisture and saliva to exhibit elasticity after sticking, and further the property of remaining on the stuck site for a long period are suitably exerted.

Other polymers are not particularly limited, but examples thereof preferably include carboxymethylcellulose, hydroxypropylcellulose, methylcellulose, ethylcellulose, hydroxypropylmethylcellulose, cellulose nanofiber, crystalline cellulose, polyacrylic acid, polyvinylpyrrolidone, polyvinyl alcohol, carrageenan, pullulan, gelatin, collagen, agarose, alginic acid, dihydric alginate of calcium or the like, gum arabic, gum tragacanth, guar gum, chitosan, chitin derivative, chitosan derivative, chondroitin sulfate, proteoglycan and the like from the viewpoints that while the handleability of the oral mucosa patch is improved, the excellent stickability of sticking to the oral mucosa even when there is a lot of moisture and saliva on the oral mucosa surface, the property of enhancing the physical protective effect for the stuck site by impregnating moisture and saliva to exhibit elasticity after sticking, and further the property of remaining on the stuck site for a long period are suitably exerted. Above all, carboxymethylcellulose, hydroxypropylcellulose, cellulose nanofiber, polyacrylic acid, agarose, and dihydric alginate of calcium or the like are more preferable as the other polymers. Each of the other polymers may be used alone or in combination of two or more kinds.

In the oral mucosa patch according to the present invention, the content of the hyaluronic acid contained in the lyophilizate per unit area is not particularly limited, but is e.g. 0.1 mg/cm$^2$ or more, preferably about 0.5 to 100 mg/cm$^2$, more preferably about 1 to 50 mg/cm$^2$, even more preferably about 2 to 25 mg/cm$^2$, still more preferably about 3 to 25 mg/cm$^2$, particularly preferably about 3 to 10 mg/cm$^2$ from the viewpoints that while the handleability of the oral mucosa patch is improved, the excellent stickability of sticking to the oral mucosa even when there is a lot of moisture and saliva on the oral mucosa surface, the property of enhancing the physical protective effect for the stuck site by impregnating moisture and saliva to exhibit elasticity after sticking, and further the property of remaining on the stuck site for a long period are suitably exerted.

The content of the polymers contained in the lyophilizate is not particularly limited as long as the content is 20 mass % or more, but is preferably 30 mass % or more, more preferably 50 mass % or more, even more preferably 65 mass % or more, still more preferably 75 mass % or more from the viewpoints that while the handleability of the oral mucosa patch is improved, the excellent stickability of sticking to the oral mucosa even when there is a lot of moisture and saliva on the oral mucosa surface, the property of enhancing the physical protective effect for the stuck site by impregnating moisture and saliva to exhibit elasticity after sticking, and further the property of remaining on the stuck site for a long period are suitably exerted. Note that the content of the polymers contained in the lyophilizate may be substantially 100 mass %.

In addition to the polymers, other components may be further contained in the lyophilizate. The other components are not particularly limited as long as the effect of the present invention is not inhibited, but examples thereof include sugars, polyhydric alcohols, acids (acids different from hyaluronic acid), and the like.

At least one of a sugar and a polyhydric alcohol is contained in the lyophilizate, so that the elasticity of the lyophilizate is enhanced and handleability of the oral mucosa patch is further improved. In addition, the gelled matter formed by impregnating moisture and saliva after sticking exhibits better elasticity and further enhances the physical protective effect for the stuck site. Under that condition, effects for suitably exerting the excellent stickability of sticking to the oral mucosa even when there is a lot of moisture and saliva on the oral mucosa surface and the property of remaining on the stuck site for a long period can be expected.

In addition, the lyophilizate contains an acid, so that the gelled matter formed by impregnating moisture and saliva after sticking exhibits better elasticity to further enhance the physical protective effect for the stuck site. Under that condition, effects for more suitably exerting the excellent stickability of sticking to the oral mucosa even when there is a lot of moisture and saliva on the oral mucosa surface, and the property of remaining on the stuck site for a long period can be expected.

The sugar is not particularly limited, but examples thereof include glucose, fructose, xylitol, sorbitol, mannitol, trehalose, lactose, maltose, sucrose, raffinose, oligosaccharide (fructooligosaccharide, galactooligosaccharide, mannan oligosaccharide, oligosaccharide of lactose and fructose, isomaltooligosaccharide, maltooligosaccharide, soybean oligosaccharide, xylooligosaccharide, etc.), α-cyclodextrin, β-cyclodextrin, γ-cyclodextrin, dextrin and the like. Each of the sugars may be used alone or in combination of two or more kinds. Note that, in the present invention, the term "sugar" does not include liquid polyhydric alcohol at 25° C., and the liquid polyhydric alcohol is included in the "polyhydric alcohol" described later.

In addition, the polyhydric alcohol is not particularly limited, but examples thereof include preferably a glycerol such as glycerol and diglycerol; a propyleneglycol such as propyleneglycol and dipropyleneglycol; 1,3-propanediol, butanediol (1,3-butanediol, 1,4-butanediol etc.), 1,2-pentanediol, 1,2-hexanediol and 1,2-octanediol; an ethyleneglycol such as ethyleneglycol, diethyleneglycol, triethyleneglycol and polyethyleneglycol; and the like, more preferably glycerol, diglycerol, propyleneglycol, 1,3-butanediol, polyethyleneglycol 200, polyethyleneglycol 400, polyethyleneglycol 600, polyethyleneglycol 1000, polyethyleneglycol 1500, polyethyleneglycol 6000, polyethyleneglycol 20000, 1,3-propanediol, 1,2-pentanediol 1,2-hexanediol, and the like. Above all, glycerol, diglycerol, polyethyleneglycol having a molecular weight of less than 1000, and the like are particularly preferable. Each of the polyhydric alcohols may be used alone or in combination of two or more kinds.

The content of the sugar or polyhydric alcohol (total content when the both are contained) in the lyophilizate is not particularly limited as long as the content is 80 mass % or less, but is preferably 70 mass % or less, more preferably 50 mass % or less, even more preferably 35 mass % or less, still more preferably 25 mass % or less from the viewpoints that while the handleability of the oral mucosa patch is improved and furthermore the physical protective effect of the gelled matter formed by impregnating moisture and saliva after sticking for the stuck site is enhanced, the excellent stickability of sticking to the oral mucosa even when there is a lot of moisture and saliva on the oral mucosa surface and the property of remaining on the stuck site for a long period are suitably exerted. Note that the lower limit of the content of the sugar or polyhydric alcohol contained in the lyophilizate is normally about 1 mass %.

The acid other than hyaluronic acid is not particularly limited as long as the substance exhibits acidity by mixing with water, and any of an inorganic acid and an organic acid can be used. Examples of the inorganic acid include phosphoric acid, hydrochloric acid, sulfuric acid, nitric acid, perchloric acid, carbonic acid and the like, and above all, phosphoric acid, hydrochloric acid and sulfuric acid are preferable. In addition, examples of the organic acid include a monocarboxylic acid such as formic acid, acetic acid, propionic acid, butyric acid, isobutyric acid, valeric acid and lipoic acid; a dicarboxylic acid such as succinic acid, phthalic acid, fumaric acid, oxalic acid, malonic acid and glutaric acid; an oxycarboxylic acid such as glycolic acid, citric acid, lactic acid, pyruvic acid, malic acid tartaric acid and salicylic acid; a polyhydroxy acid such as glucono-δ-lactone and lactopionic acid; an acidic amino acid such as glutamic acid and aspartic acid; an amino acid derivative such as NAHLSGEN® (methyl carboxymethylphenyl aminocarboxypropylphosphonate); and an ascorbic acid or its derivative such as ascorbic acid, ascorbic acid ethyl and ascorbic acid glucoside, and above all, phosphoric acid, ascorbic acid, citric acid, glycolic acid, lactic acid, malic acid, tartaric acid, salicylic acid, ascorbic acid ethyl, ascorbic acid glucoside, glucono-δ-lactone, lactopionic acid and the like are preferable. Each of the acids may be used alone or in combination of two or more kinds.

The acid content in the lyophilizate is not particularly limited, but is exemplified by an amount allowing the pH value of the aqueous solution measured by the following measurement method to be within a range of 1.9 to 5.2.

(Method for Measuring pH Value)

Among the components contained in the lyophilizate fraction containing 1 g of hyaluronic acid, all ionic components are dissolved in water to prepare an aqueous solution so that the total volume is 200 mL, and the pH value of the resulting aqueous solution is measured. Note that the abovementioned sugar and polyhydric alcohol are not blended in the aqueous solution for the pH measurement because they are nonionic components.

Further examples of other components include a steroidal antiinflammatory agent such as dexamethasone and triamcinolone acetonide; an antiinflammatory agent such as glycyrrhizic acid and methyl salicylate; a wound healing agent such as sodium azulenesulfonate, allantoin, sofalcone, rebamipide and NAHLSGEN® (methyl carboxymethylphenyl aminocarboxypropylphosphonate); a bactericide such as chlorinated cetylpyridinium, cetylpyridinium chloride, chlorhexidine gluconate, povidone iodine, cineole and thymol; a zinc compound such as zinc chloride, zinc sulfate, zinc picolinate, zinc gluconate and zinc acetate; a perfume such as L-menthol; a vitamin such as vitamin B2 and vitamin E; an extracted product or an extract of an animal, a plant or a herbal medicine; and an active ingredient such as bloodstream promoter. Each of these other components may be used alone or in combination of two or more kinds.

The oral mucosa patch according to the present invention has the excellent stickability of sticking to the oral mucosa even when there is a lot of moisture and saliva on the oral mucosa surface and the property of remaining on the stuck site for a long period, and thus when the oral mucosa patch according to the present invention contains active ingredients and the like, the active ingredients can be released in the oral cavity over a long period. Hence, the oral mucosa patch according to the present invention can also be used e.g. for preventing or treating oral diseases such as alveolar pyorrhea, gingivitis, stomatitis, cheilitis and oral mucositis.

The oral mucosa patch according to the present invention has the excellent stickability of sticking to the oral mucosa even when there is a lot of moisture and saliva on the oral mucosa surface and the property of allowing the dissolution time in the oral cavity to be controlled, and furthermore can be produced without heating, and thus when the oral mucosa patch according to the present invention contains an allergen protein, the oral mucosa patch can also be used for specific hyposensitization therapy applied to the oral mucosa.

In addition, the oral mucosa patch according to the present invention has the excellent stickability of sticking to the oral mucosa even when there is a lot of moisture and saliva on the oral mucosa surface and the property of remaining on the stuck site for a long period, and thus when the oral mucosa patch according to the present invention contains a systemic active ingredient or the like, the systemic active ingredient is directly transferred to the systemic circulation via the oral mucosa without passing through the liver, so that the systemic active ingredient can be efficiently absorbed in a body. Consequently, the oral mucosa patch according to the present invention can also be used for transoral mucosally-absorbable preparation applied to the oral mucosa.

In addition, since the oral mucosa patch has the excellent stickability of sticking to the oral mucosa even when there is a lot of moisture and saliva on the oral mucosa surface, the property of enhancing the physical protective effect for the stuck site by impregnating moisture and saliva to exhibit elasticity after sticking, and further the property of remaining on the stuck site for a long period, the oral mucosa patch can also be used as a protector for damage bleeding sites of oral mucosa and gum in dental treatment or the like.

In the present invention, the thickness of the lyophilizate is not particularly limited, but when the oral mucosa patch is composed of a monolayer of the lyophilizate, the thickness is preferably about 0.05 to 10 mm. In addition, when the oral mucosa patch is a laminate composed of the lyophilizate and a base described below, the thickness of the lyophilizate is preferably about 0.02 to 10 mm. Furthermore, the lyophilizate prepared by lyophilization can also be thinned by compression to obtain an oral mucosa patch.

In the present invention, the area of the adherend surface with the oral mucosa can also be appropriately set depending on the application site or the like, and the area is e.g. about 0.2 to 50 cm$^2$. Also, the shape of the adherend surface with the oral mucosa is not particularly limited, and examples of the shape include circle, ellipse, polygon (triangle, square, pentagon, hexagon, etc.), star shape, indeterminate shape and the like.

Figure 1:
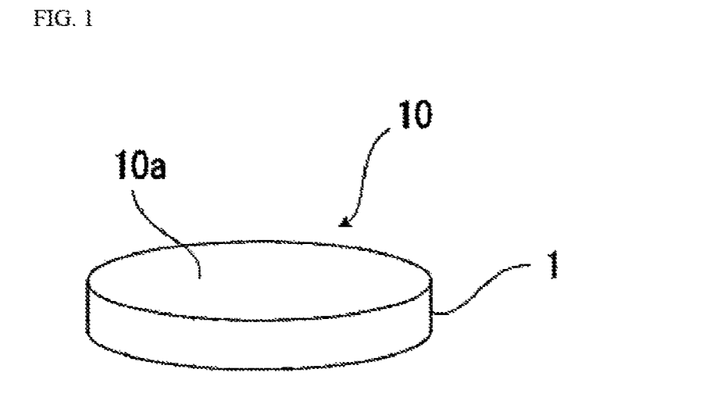
FIG. 1 shows a schematic configuration of the oral mucosa patch according to the present invention.
Figure 2:
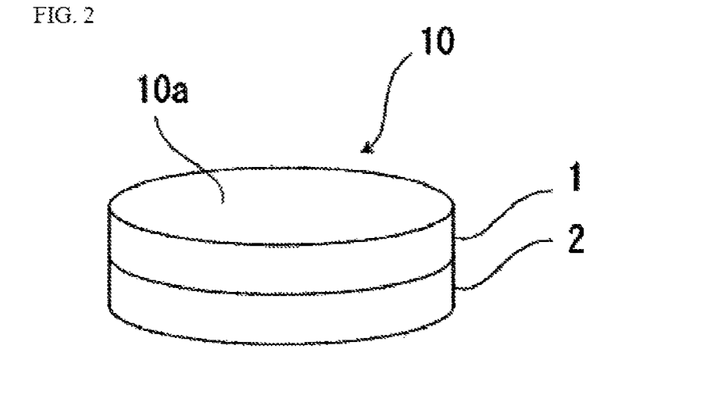
FIG. 2 shows a schematic configuration of the oral mucosa patch according to the present invention.

For example, as shown in FIG. 1, an oral mucosa patch 10 according to the present invention may be composed of a monolayer of a lyophilizate 1, or e.g. as shown in FIG. 2, composed of a bilayer of a base 2 and the lyophilizate 1 laminated on the base 2. In FIG. 1 and FIG. 2, the surface of the lyophilizate 1 constitutes an adherend surface 10a with the oral mucosa.

The oral mucosa patch according to the present invention has a base, so that while handleability of the oral mucosa patch can be further improved, effects for suitably exerting the excellent stickability of sticking to the oral mucosa even when there is a lot of moisture and saliva on the oral mucosa surface and the property of remaining in the oral cavity for a long period can be expected. For example, as a material constituting the base, a base having high mechanical strength and high water resistance and having a stickability to a moist hand or the like inferior to that of the lyophilizate containing hyaluronic acid is used, so that such effects can be suitably exhibited.

The material constituting the base is not particularly limited, but, from the viewpoint of exerting such effects, the aforementioned other polymers and the other polymers blended with a polyhydric alcohol or the like are preferable. Such effects can be suitably exhibited e.g. by using a lyophilizate of the aforementioned other polymer as a base. Particularly preferable examples of the material constituting the base include a lyophilizate of an aqueous solution containing the other polymers such as methylcellulose, hydroxypropylmethylcellulose, cellulose nanofiber, agarose and dihydric alginate of calcium or the like, and a lyophilizate of an aqueous solution containing these polymers and polyethyleneglycol having a molecular weight of 1000 or more. Each of the other polymers may be used alone or in combination of two or more kinds including hyaluronic acid (less than 50%).

In addition, a thin film made of hyaluronic acid and the aforementioned other polymer is used as a base, so that such effects can be suitably exhibited. Examples of the material constituting the base include hyaluronic acid, the aforementioned other polymers, a biodegradable polymer such as polylactic acid, and the other polymers blended with a plasticizer such as a polyhydric alcohol. Each of hyaluronic acid, the other polymers and the plasticizers to be added may be used alone or in combination of two or more kinds.

When the oral mucosa patch according to the present invention has a base, the thickness of the base is not particularly limited, but is preferably 0.0001 to 10 mm, more preferably 0.0002 to 5 mm, or 0.01 to 10 mm.

Since the oral mucosa patch according to the present invention can suitably protect the oral mucosa surface, the oral mucosa patch can be suitably used for preventing or treating oral mucosal diseases. The oral mucosal diseases are not particularly limited, and exemplified by diseases resulting from stomatitis, cancer treatment and the like.

The application site of the oral mucosa patch according to the present invention is not particularly limited as long as the site is an oral mucosa. In addition, eating and drinking are allowed in a state that the oral mucosa patch according to the present invention is stuck to the oral mucosa.

The method for producing an oral mucosa patch according to the present invention is not particularly limited, but is exemplified by a method including preparing an aqueous solution containing the aforementioned polymer and lyophilizing the aqueous solution, and using a polymer containing 50 mass % or more of hyaluronic acid as the polymer.

In the method for producing an oral mucosa patch according to the present invention, details of the hyaluronic acid and other polymer, contents of each component and the like are as described above. Also, the contents of the other polymer and the hyaluronic acid in the aqueous solution containing the polymers should be adjusted so as to be the same as in the aforementioned oral mucosa patch.

When the oral mucosa patch according to the present invention is composed of a bilayer including a base and a lyophilizate laminated on the base, e.g. when the base is composed of the lyophilizate of the aforementioned other polymer, a bi-layered oral mucosa patch can be produced by a method in which any one of the aqueous solution of the other polymer and the aqueous solution of the hyaluronic acid-containing polymer is frozen, the other aqueous solution is poured to the lyophilizate placed in a container and frozen, and then the both aqueous solutions are lyophilized. In addition, e.g. when the base is composed of the film of the aforementioned other polymer, a method in which the aqueous solution of the hyaluronic acid-containing polymer is poured into a container, on which the film is overlaid, frozen, and then lyophilized is used.

In addition, the bi-layered oral mucosa patch can be produced e.g. by laminating the hyaluronic acid-containing polymer aqueous solution on the base placed in the container and lyophilizing the polymer aqueous solution in that state.

EXAMPLES

Hereinafter, the present invention will be explained in detail with reference to examples and comparative examples. However, the present invention is not limited to examples. Note that the reagents used in the following examples and comparative examples are as follows.

Reagents

Hyaluronic acid (2,300,000): Sodium hyaluronate, Trade name "HYALURONSAN HA-LQSH" made by Kewpie Corporation (Product labeling: molecular weight 1,600,000 to 2,900,000, average molecular weight 2,300,000, intrinsic viscosity 25.0 to 40.0 dL/g)

Hyaluronic acid (1,600,000): Sodium hyaluronate, Trade name "HYALURONSAN HA-LQH" made by Kewpie Corporation (Product labeling: molecular weight 1,200,000 to 2,200,000, average molecular weight 1,600,000, intrinsic viscosity 19.5 to 32.0 dL/g)

Hyaluronic acid (1,200,000): Sodium hyaluronate, Trade name "HYALURONSAN HA-LQ" made by Kewpie Corporation (Product labeling: molecular weight 85 to 1,600,000, average molecular weight 1,200,000, intrinsic viscosity 15.0 to 25.0 dL/g)

Hyaluronic acid (600,000): Sodium hyaluronate, Trade name "HYALURONIC ACID FCH-60" made by Kikkoman Biochemifa Company (Product labeling: average molecular weight 500,000 to 700,000)

Hyaluronic acid (350,000): Hyaluronic acid, Trade name "HYALURONSAN HA-LF-P" made by Kewpie Corporation (Product labeling: molecular weight 200,000 to 500,000, average molecular weight 350,000) (Measured intrinsic viscosity value of a reagent used in EXAMPLES: 8.7 dL/g)

Hyaluronic acid (100,000): Sodium hyaluronate, Trade name "HYALURONIC ACID FCH-SU" made by Kikkoman Biochemifa Company (Product labeling: average molecular weight 50,000 to 110,000)

Carboxymethylcellulose: sodium carboxycellulose, trade name "CELLOGEN F-BSH-12" made by DKS Co. Ltd.

Methylcellulose: Trade name "METHYLCELLULOSE SM-4000" made by Shin-Etsu Chemical Co., Ltd.

Hydroxypropylmethylcellulose: Trade name "HYPROMELLOSE 65SH-4000" made by Shin-Etsu Chemical Co., Ltd.

Hydroxypropylcellulose: Trade name "HYDROXYPROPYLCELLULOSE H" made by NIPPON SODA CO., LTD.

Polyacrylic acid: Trade name "Poly(acrlic acid): Average molecular weight: 1,250,000 or less" made by Sigma-Aldrich Co. LLC.

Polyvinylpyrrolidone: Trade name "POLYVINYLPYRROLIDONE K90 (for molecular biology)" made by Wako Pure Chemical Industries, Ltd.

Pullulan: Pullulan (for biochemistry) made by Wako Pure Chemical Industries, Ltd.

Cellulose nanofiber: Trade name "RHEOCRYSTA (antiseptic-free)" made by DKS Co. Ltd.

Gum arabic: Gum arabic (reagent) made by Wako Pure Chemical Industries, Ltd.

Gelatin: Trade name "GELATIN 21" made by Nitta Gelatin Inc.

Xylitol: Xylitol (special grade) made by Wako Pure Chemical Industries, Ltd.

Sorbitol: D(+)-sorbitol (first class grade) made by Wako Pure Chemical Industries, Ltd.

Trehalose: Trehalose dihydrate (special grade) made by Wako Pure Chemical Industries. Ltd.

Isomaltooligosaccharide: Trade name "PANORUP" made by Hayashibara Co., Ltd.

Oligosaccharide of lactose and fructose: Trade name "NYUKA OLIGO 700" made by Hayashibara Co., Ltd.

Galactooligosaccharide: Trade name "OLIGOMATE 55N" made by Yakult Pharmaceutical Industry Co., Ltd.

Xylooligosaccharide: Trade name "XYLOOLIGOSACCHARIDE 70L" made by B Food Science Co., Ltd.

Fructooligosaccharide: Trade name "MEIOLIGO P (liquid)" made by Meiji Food Materia Co., Ltd.

Glycerol: Glycerin (special grade) made by Wako Pure Chemical Industries, Ltd.

Diglycerol: Diglycerol (for gas chromatograph) made by Wako Pure Chemical Industries, Ltd.
Phosphoric acid: Phosphoric acid (special grade) made by Wako Pure Chemical Industries, Ltd.
Citric acid: Citric acid (special grade) made by Wako Pure Chemical Industries, Ltd.
Lactic acid: DL-lactic acid (special grade) made by Wako Pure Chemical Industries, Ltd.
Vitamin C: L(+)-ascorbic acid (special grade) made by Wako Pure Chemical Industries, Ltd.
Proteoglycan: Trade name "PROTEOGLYCAN F" made by ICHIMARU PHARCOS Co., Ltd.
Hyaluronic acid (600,000; HA-LQ60): Sodium hyaluronate, Trade name "HYALURONSAN HA-LQ60" made by Kewpie Corporation (Product labeling: molecular weight 500,000 to 750,000, average molecular weight 600,000, intrinsic viscosity 10.0 to 14.0 dL/g)
Hyaluronic acid (800,000; HYABEST (J)): Sodium hyaluronate, Trade name "HYABEST (J)" made by Kewpie Corporation (Product labeling: molecular weight 600,000 to 1,200,000, average molecular weight 800,000) (Measured intrinsic viscosity value of a reagent used in examples: 14.1 dL/g)
Sodium carboxymethyl hyaluronate: Trade name "HYALO-CATCH" made by Kewpie Corporation (Product labeling: molecular weight 800,000 to 1,200,000)
Agarose: AGAROSE III made by Wako Pure Chemical Industries. Ltd.
Alginic acid: sodium alginate 500-600 made by Wako Pure Chemical Industries, Ltd. (first class grade)
Crystalline cellulose: Trade name "CEOLUS KG-1000" made by Asahi Kasei Corporation
Mannitol: D(−)-mannitol (special grade) made by Wako Pure Chemical Industries, Ltd.
Polyethyleneglycol 1000: Polyethyleneglycol 1000 (lumpy) made by Wako Pure Chemical Industries. Ltd.
Polyethyleneglycol 400: Polyethyleneglycol 400 (first class grade) made by Wako Pure Chemical Industries. Ltd.
Calcium chloride: Calcium chloride (special grade) made by Wako Pure Chemical Industries, Ltd.
Polylactic acid film: Polylactic acid film made by TSUKIOKA FILM PHARMA CO., LTD. (thickness: 0.0002 mm)

Examples 1 to 6

Production of the Oral Mucosa Patch

Each of the hyaluronic acids having molecular weights described in Table 1 was uniformly dissolved in water to prepare each hyaluronic acid aqueous solution. At this time, a hyaluronic acid concentration in each hyaluronic acid aqueous solution was 10 mg/ml. Subsequently, the resulting hyaluronic acid aqueous solution was put into a plastic petri dish having a base area of 9.1 cm$^2$ so that the hyaluronic acid content per unit area was 7.5 mg/cm$^2$, and frozen in a freezer at −82° C. Then, the hyaluronic acid aqueous solution was lyophilized in the petri dish at a pressure of 10 Pa or lower (24 hours) to obtain a lyophilizate of the hyaluronic acid. The resulting lyophilizate was used as an oral mucosa patch. The thickness of each oral mucosa patch was about 0.75 cm.

Evaluation for Property of the Oral Mucosa Patch

The properties of the oral mucosa patch were evaluated in accordance with the following criteria. The results are shown in Table 1.

Property of the Oral Mucosa Patch

A: a cotton-like dried matter, which is fluffy and inelastic.
B: a cotton-like dried matter, which is fluffy but elastic.
C: a cotton-like dried matter, which is less flexible but elastic.
D: a high-density spongy dried matter, which is less flexible.
E: a cotton-like dried matter, which is fragile.

Evaluation for States of Sticking to and Remaining on the Oral Mucosa

Each oral mucosa patch obtained above was cut with a 20 mmφ punch, and the each patch was stuck to an oral mucosa (inside of cheek in the oral cavity, in a state that the oral mucosa surface was very moist) cleaned by rinsing an oral cavity with 100 ml of distilled water. The patch was allowed to stand as it was for 10 minutes, then the oral cavity was rinsed with 100 ml of distilled water, and after 30 minutes, the oral cavity was further rinsed with 100 ml of distilled water, and the sticking state 10 minutes after the sticking (sticking property) and the state of the oral mucosa patch remaining after two rinses with distilled water were evaluated in accordance with the following criteria. The results are shown in Table 1.

Evaluation Criteria for the Sticking State 10 Minutes after Sticking

A: The oral mucosa patch was firmly stuck to the oral mucosa, and the oral mucosa patch could be hydrated to suitably protect the oral mucosa. Furthermore, the oral mucosa patch was not almost dissolved out.
B: The oral mucosa patch was stuck and the oral mucosa patch could be hydrated to protect the oral mucosa, but the oral mucosa patch was dissolved out.
C: At the time of sticking, the oral mucosa patch was firmly stuck to the oral mucosa, but the oral mucosa patch was hydrated, almost all of which was dissolved out, and the oral mucosa could not be protected.
D: At the time of sticking, the patch was not almost stuck to the oral mucosa, and after 10 minutes, the patch was peeled from the oral mucosa.

Evaluation Criteria for State of the Oral Mucosa Patch Remaining after Two Rinses with Distilled Water A: Even after rinsing, most of the hydrated oral mucosa patch remained, and the oral mucosa could be suitably protected.
B: After rinsing, the hydrated oral mucosa patch was reduced compared to the patch 10 minutes after sticking, but the oral mucosa could be protected.
C: After rinsing, the hydrated oral mucosa patch was considerably reduced compared to the patch 10 minutes after sticking, but the oral mucosa could be protected.
D: After rinsing, the hydrated oral mucosa patch completely disappeared.

TABLE 1

| | Molecular weight of hyaluronic acid | Property | Stickability | Remaining state |
|---|---|---|---|---|
| Example 1 | 2,300,000 | A | A | A |
| Example 2 | 1,600,000 | A | A | A |

TABLE 1-continued

|  | Molecular weight of hyaluronic acid | Property | Stickability | Remaining state |
|---|---|---|---|---|
| Example 3 | 1,200,000 | A | A | A |
| Example 4 | 600,000 | A | A | B |
| Example 5 | 350,000 | A | A | C |
| Example 6 | 100,000 | A | B | D |

Examples 7 to 14

Production of the Oral Mucosa Patch

Each oral mucosa patch was obtained in the same manner as in Examples 1 to 6 except that each hyaluronic acid (molecular weight: 2,300,000) was uniformly dissolved in 9.1 ml of distilled water in a plastic petri dish (base area: 9.1 cm$^2$) so that the hyaluronic acid content per unit area was the value described in Table 2 and frozen in a freezer at −82° C. The thickness of each oral mucosa patch was about 1.0 cm. Subsequently, the property of each oral mucosa patch, the states of sticking to and remaining on the oral mucosa were evaluated in the same manner as in Examples 1 to 6. The results are shown in Table 2.

TABLE 2

|  | Content of hyaluronic acid (mg/cm$^2$) | Property | Stickability | Remaining state |
|---|---|---|---|---|
| Example 7 | 1 | A | A | C |
| Example 8 | 2 | A | A | B |
| Example 9 | 3 | A | A | A |
| Example 10 | 5 | A | A | A |
| Example 11 | 10 | B | A | A |
| Example 12 | 25 | C | A | A |
| Example 13 | 50 | D | A | A |
| Example 14 | 100 | D | A | A |

Examples 15 to 24

Production of the Oral Mucosa Patch

The hyaluronic acid (molecular weight: 2,300,000) and each of other polymers shown in Table 3 (polymer different from the hyaluronic acid) were uniformly dissolved in water to prepare each aqueous solution so that the hyaluronic acid content was 80 mass % and the other polymer content was 20 mass %. At this time, a total concentration of the hyaluronic acid and the other polymer in each aqueous solution was 10 mg/ml. The resulting hyaluronic acid aqueous solution was put into a plastic petri dish having a base area of 9.1 cm$^2$ so that the polymer content including the hyaluronic acid per unit area was 7.5 mg/cm$^2$, and frozen in a freezer at −82° C. Then, the hyaluronic acid aqueous solution was lyophilized in the petri dish at a pressure of 10 Pa or lower (24 hours) to obtain a lyophilizate. The resulting lyophilizate was used as an oral mucosa patch. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 3.

TABLE 3

|  | Other polymer (Content: 20 mass %) | Property | Stickability | Remaining state |
|---|---|---|---|---|
| Example 15 | Carboxymethyl-cellulose | B | A | A |
| Example 16 | Hydroxypropyl-cellulose | A | A | A |
| Example 17 | Methylcellulose | B | A | A |
| Example 18 | Hydroxypropyl-methylcellulose | B | A | A |
| Example 19 | Cellulose nanofiber | C | A | A |
| Example 20 | Polyacrylic acid | C | A | A |
| Example 21 | Poly-vinylpyrrolidone | B | A | B |
| Example 22 | Pullulan | B | A | B |
| Example 23 | Gelatin | B | A | A |
| Example 24 | Gum arabic | A | A | B |

Examples 25 to 28

Production of the Oral Mucosa Patch

Each oral mucosa patch was obtained in the same manner as in Examples 15 to 24 except that the hyaluronic acid (molecular weight: 2,300,000) and each of other polymers shown in Table 4 were uniformly dissolved in water to prepare each aqueous solution so that the hyaluronic acid content was 50 mass % and the other polymer content was 50 mass %. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 4.

TABLE 4

|  | Other polymer (Content: 50 mass %) | Property | Stickability | Remaining state |
|---|---|---|---|---|
| Example 25 | Carboxymethylcellulose | B | A | A |
| Example 26 | Hydroxypropylcellulose | B | A | A |
| Example 27 | Polyacrylic acid | C | A | A |
| Example 28 | Gelatin | C | A | A |

Comparative Example 1

Production of the Oral Mucosa Patch

The hyaluronic acid (molecular weight: 2,300,000) was uniformly dissolved in water to prepare an aqueous solution with a hyaluronic acid concentration of 20 mg/ml. The resulting hyaluronic acid aqueous solution was put into a plastic petri dish having a base area of 9.1 cm$^2$ so that the hyaluronic acid content per unit area was 10 mg/cm$^2$, and dried in a thermostat at 80° C. for 4 hours to obtain a transparent and slightly hard hyaluronic acid film body. The resulting film body was used as an oral mucosa patch. The thickness of the oral mucosa patch was about 60 μm.

Comparative Example 2

Production of the Oral Mucosa Patch

A tablet of hyaluronic acid (molecular weight: 2,300,000) was obtained by using a telegraph TG-50KN (made by Minebea Co., Ltd.) and a tableting jig at a pressure of 24

$KN/cm^2$. The resulting tablet was used as an oral mucosa patch. The tablet had a mass of 150 mg, a size of 10 mmφ and a thickness of about 3 mm.

Comparative Example 3

A bulk (powder) of hyaluronic acid (molecular weight: 2,300,000) was directly used as an oral mucosa patch.

State of Sticking to the Oral Mucosa in Comparative Examples 1 to 3

The oral mucosa patch (film) in Comparative Example 1 which was cut with a 20 mmφ punch, the oral mucosa patch (tablet) in Comparative Example 2 which received no treatment, and 25 mg of the oral mucosa patch (powder) in Comparative Example 3 which received no treatment, were stuck to the oral mucosa (inside of cheek in the oral cavity, in a state that the oral mucosa surface was very moist) cleaned by rinsing an oral cavity with 100 ml of distilled water. However, although all oral mucosa patches in Comparative Examples 1 to 3 were hydrated, they were not stuck to the oral mucosa, and after 10 minutes, they were peeled from the oral mucosa.

Comparative Examples 4 to 13

Production of the Oral Mucosa Patch

Each oral mucosa patch containing no hyaluronic acid was obtained in the same manner as in Examples 15 to 24 except that each polymer shown in Table 5 was uniformly dissolved in water so that the polymer content was 100 mass % and the polymer concentration was 10 mg/ml. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 5.

TABLE 5

| | Other polymer (Content: 100 mass %) | Property | Stickability | Remaining state |
|---|---|---|---|---|
| Comparative Example 4 | Carboxymethylcellulose | C | A | B |
| Comparative Example 5 | Hydroxypropylcellulose | B | A | C |
| Comparative Example 6 | Methylcellulose | A | D | — |
| Comparative Example 7 | Hydroxypropyl-methylcellulose | A | D | — |
| Comparative Example 8 | Cellulose nanofiber | C | D | — |
| Comparative Example 9 | Polyacrylic acid | B | A | C |
| Comparative Example 10 | Polyvinylpyrrolidone | A | B | D |
| Comparative Example 11 | Pullulan | E | C | D |
| Comparative Example 12 | Gelatin | B | A | C |
| Comparative Example 13 | Gum arabic | E | C | D |

After the oral mucosa patch was stuck to the oral mucosa and rinsed twice with distilled water, the properties of the remaining patches in Comparative Examples 4, 5, 9 and 12 are as shown in Table 5. Specifically, the patch in Comparative Example 4 was an elastic and thixotropic gelled matter which was liable to disintegrate by touch with a tongue. The patches in Comparative Examples 5, 9 and 12 were viscous matters. On the other hand, the patch in Example 1 which remained after rinsing twice with distilled water was a gelled matter having good elasticity.

Examples 29 to 35

Production of the Oral Mucosa Patch

The hyaluronic acid (molecular weight: 2,300,000) and each of acids were uniformly dissolved in water to prepare each aqueous solution so that the hyaluronic acid content and the acid content were at the percentages (mass %) described in Table 6. At this time, the hyaluronic acid concentration in each aqueous solution was 10 mg/ml. The resulting hyaluronic acid aqueous solution was put into a plastic petri dish having a base area of 9.1 $cm^2$ so that the hyaluronic acid content per unit area was 7.5 $mg/cm^2$, and frozen in a freezer at −82° C. The hyaluronic acid aqueous solution was lyophilized in the petri dish at a pressure of 10 Pa or lower (24 hours) to obtain a lyophilizate of the acid-containing hyaluronic acid. The resulting lyophilizate was used as an oral mucosa patch. The thickness of each oral mucosa patch was about 0.75 cm. Subsequently, the property of each oral mucosa patch, the states of each oral mucosa patch sticking to and remaining on the oral mucosa were evaluated in the same manner as in Examples 1 to 6. The results are shown in Table 6. Since the oral mucosa patches in Examples 29 to 35 contained the acids in the lyophilizate, the oral mucosa patches (gelled matter) 10 minutes after sticking exhibited high elasticity.

TABLE 6

| | Hyaluronic acid and acid, and their contents (mass %) | Property | Stickability | Remaining state |
|---|---|---|---|---|
| Example 29 | Hyaluronic acid; 90%, Citric acid; 10% | B | A | A |
| Example 30 | Hyaluronic acid; 50%, Citric acid; 50% | B | A | A |
| Example 31 | Hyaluronic acid; 75%, Lactic acid; 25% | A | A | A |
| Example 32 | Hyaluronic acid; 75%, Vitamin C; 25% | B | A | A |
| Example 33 | Hyaluronic acid; 50%, Vitamin C; 50% | B | A | A |
| Example 34 | Hyaluronic acid; 90%, Phosphoric acid; 10% | A | A | A |
| Example 35 | Hyaluronic acid; 75%, Phosphoric acid; 25% | B | A | A |

Examples 36 to 48

Production of the Oral Mucosa Patch

The hyaluronic acid (molecular weight: 2,300,000) and each of sugars/polyhydric alcohols were uniformly dissolved in water to prepare each aqueous solution so that the hyaluronic acid content and the sugar/polyhydric alcohol content were at the percentages (mass %) described in Table 7. At this time, the hyaluronic acid concentration in each aqueous solution was 10 mg/ml. The resulting hyaluronic acid aqueous solution was put into a plastic petri dish having a base area of 9.1 cm$^2$ so that the hyaluronic acid content per unit area was 7.5 mg/cm$^2$, and frozen in a freezer at −82° C. Then, the hyaluronic acid aqueous solution was lyophilized in the petri dish at a pressure of 10 Pa or lower (for 24 hours) to obtain a lyophilizate of the sugar/polyhydric alcohol-containing hyaluronic acid. The resulting lyophilizate was used as an oral mucosa patch. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 7. Since the oral mucosa patches in Examples 36 to 48 contained the sugars in the lyophilizate, the properties of the oral mucosa patches included elasticity, and the handleability was further improved. In addition, the oral mucosa patches (gelled matter) 10 minutes after sticking exhibited high elasticity.

TABLE 7

| | Contents of hyaluronic acid and sugar/ polyhydric alcohol (mass %) | Property | Stickability | Remaining state |
|---|---|---|---|---|
| Example 36 | Hyaluronic acid; 75% Xylitol; 25% | B | A | A |
| Example 37 | Hyaluronic acid; 75% Sorbitol; 25% | B | A | A |
| Example 38 | Hyaluronic acid; 75% Glycerol; 25% | A | A | A |
| Example 39 | Hyaluronic acid; 75% Diglycerol; 25% | A | A | A |
| Example 40 | Hyaluronic acid; 75% Trehalose; 25% | B | A | A |
| Example 41 | Hyaluronic acid; 75% Xylooligosaccharide; 25% | B | A | A |
| Example 42 | Hyaluronic acid; 75% Isomaltooligosaccharide; 25% | B | A | A |
| Example 43 | Hyaluronic acid; 75% Fructooligosaccharide; 25% | B | A | A |
| Example 44 | Hyaluronic acid; 75% Oligosaccharide of lactose and fructose; 25% | B | A | A |
| Example 45 | Hyaluronic acid; 90% Galactooligosaccharide; 10% | B | A | A |
| Example 46 | Hyaluronic acid; 75% Galactooligosaccharide; 25% | B | A | A |
| Example 47 | Hyaluronic acid; 50% Galactooligosaccharide; 50% | B | A | A |
| Example 48 | Hyaluronic acid; 20% Galactooligosaccharide; 80% | C | A | A |

Examples 49 to 52

Production of the Oral Mucosa Patch

The hyaluronic acid (molecular weight: 2,300,000), each of other polymers and galactooligosaccharide were uniformly dissolved in water to prepare each aqueous solution so that the hyaluronic acid content, the other polymer content and the galactooligosaccharide content were at the percentages (mass %) described in Table 8. At this time, a total concentration of the hyaluronic acid and the other polymer in each aqueous solution was 10 mg/ml. The resulting hyaluronic acid aqueous solution was put into a plastic petri dish having a base area of 9.1 cm$^2$ so that the polymer content including the hyaluronic acid per unit area was 7.5 mg/cm$^2$, and frozen in a freezer at −82° C. Then, the hyaluronic acid aqueous solution was lyophilized in the petri dish at a pressure of 10 Pa or lower (24 hours) to obtain a lyophilizate of the hyaluronic acid containing the other polymer and galactooligosaccharide. The resulting lyophilizate was used as an oral mucosa patch. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 8. Since the oral mucosa patches in Examples 49 to 52 contained the sugars in the lyophilizate, the properties of the oral mucosa patches included elasticity, and the handleability was further improved. In addition, the oral mucosa patches (gelled matter) 10 minutes after sticking exhibited high elasticity.

TABLE 8

|  | Contents of hyaluronic acid, other polymer and sugar/polyhydric alcohol (mass %) | Property | Stickability | Remaining state |
| --- | --- | --- | --- | --- |
| Example 49 | Hyaluronic acid; 10% Carboxymethylcellulose; 10% Galactooligosaccharide; 80% | C | A | A |
| Example 50 | Hyaluronic acid; 10% Hydroxypropylcellulose; 10% Galactooligosaccharide; 80% | C | A | A |
| Example 51 | Hyaluronic acid; 10% Polyacrylic acid; 10% Galactooligosaccharide; 80% | C | A | A |
| Example 52 | Hyaluronic acid; 40% Proteoglycan; 15% Dextrin; 45% | C | A | A |

Examples 53 to 62

Production of the Oral Mucosa Patch

The hyaluronic acid (molecular weight: 2,300,000), each of sugars and each of acids were uniformly dissolved in water to prepare each aqueous solution so that the hyaluronic acid content, the sugar content and the acid content were at the percentages (mass %) described in Table 9. At this time, the hyaluronic acid concentration in each aqueous solution was 10 mg/ml. The resulting hyaluronic acid aqueous solution was put into a plastic petri dish having a base area of 9.1 cm$^2$ so that the hyaluronic acid content per unit area was 7.5 mg/cm$^2$, and frozen in a freezer at −82° C. Then, the hyaluronic acid aqueous solution was lyophilized in the petri dish at a pressure of 10 Pa or lower (24 hours) to obtain a lyophilizate of the hyaluronic acid containing the acid and the sugar. The resulting lyophilizate was used as an oral mucosa patch. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 9. Since the oral mucosa patches in Examples 53 to 62 contained the sugars and the acids in the lyophilizate, the properties of the oral mucosa patches included elasticity, and the handleability was further improved. In addition, the oral mucosa patches (gelled matter) 10 minutes after sticking exhibited high elasticity.

TABLE 9

| | Contents of hyaluronic acid, acid and sugar/polyhydric alcohol (mass %) | Property | Stickability | Remaining state |
|---|---|---|---|---|
| Example 53 | Hyaluronic acid; 50%<br>Citric acid; 25%<br>Xylitol; 25% | B | A | A |
| Example 54 | Hyaluronic acid; 50%<br>Citric acid; 25%<br>Trehalose; 25% | B | A | A |
| Example 55 | Hyaluronic acid; 70%<br>Citric acid; 10%<br>Galactooligosaccharide; 20% | B | A | A |
| Example 56 | Hyaluronic acid; 40%<br>Citric acid; 40%<br>Galactooligosaccharide; 20% | B | A | A |
| Example 57 | Hyaluronic acid; 50%<br>Citric acid; 25%<br>Glycerol; 25% | A | A | A |
| Example 58 | Hyaluronic acid; 50%<br>Lactic acid; 25%<br>Galactooligosaccharide; 25% | B | A | A |
| Example 59 | Hyaluronic acid; 50%<br>Vitamin C; 25%<br>Galactooligosaccharide; 25% | B | A | A |
| Example 60 | Hyaluronic acid; 65%<br>Phosphoric acid; 10%<br>Xylitol; 25% | B | A | A |
| Example 61 | Hyaluronic acid; 65%<br>Phosphoric acid; 10%<br>Trehalose; 25% | B | A | A |
| Example 62 | Hyaluronic acid; 65%<br>Phosphoric acid; 10%<br>Galactooligosaccharide; 25% | B | A | A |

Examples 63 to 65

Production of the Oral Mucosa Patch

The hyaluronic acid (molecular weight: 2,300,000) was uniformly dissolved in water to prepare an aqueous solution with a hyaluronic acid concentration of 10 mg/ml. Subsequently, the resulting hyaluronic acid aqueous solution was put into a plastic petri dish having a base area of 9.1 cm$^2$ so that the hyaluronic acid content per unit area was 7.5 mg/cm$^2$, and frozen in a freezer at −82° C. Subsequently, each of polymers described in Table 10 was uniformly dissolved in water to prepare each aqueous solution with a polymer concentration of 10 mg/ml so that the polymer content was 100 mass %, which was put on the lyophilized hyaluronic acid aqueous solution so that the polymer content was 2.0 mg/cm$^2$ and frozen in a freezer at −82° C. Then, this frozen aqueous solution was lyophilized in the petri dish at a pressure of 10 Pa or lower (24 hours) to obtain an oral mucosa patch composed of two layers of the lyophilizate/base. The thickness of each oral mucosa patch was about 0.95 cm. Subsequently, the property of each oral mucosa patch, the states of sticking to and remaining on the oral mucosa were evaluated in the same manner as in Examples 1 to 6. The results are shown in Table 10. Since the oral mucosa patches in Examples 61 to 63 had a configuration that the hyaluronic acid-containing lyophilizate was laminated on the other polymer layer (base) with low stickability for the oral mucosa, the patch did not adhere to the lyophilizate as the base even with wet hands when sticking the oral mucosa patch to the oral mucosa, and was particularly excellent in applicability for the oral cavity.

TABLE 10

| | Other polymer used as base | Property | Stickability | Remaining state |
|---|---|---|---|---|
| Example 63 | Methylcellulose | A | A | A |
| Example 64 | Hydroxypropyl-methylcellulose | A | A | A |
| Example 65 | Cellulose nanofiber | C | A | A |

Volunteer Test for Oral Mucosa

Each oral mucosa patch prepared in Examples 63 to 65 was cut with a 20 mmϕ punch, and stuck to the oral mucosa (inside of cheek in the oral cavity) of 3 volunteers with stomatitis. After sticking, the volunteers conducted a normal life without eating and drinking. As a result, in the three volunteers, all oral mucosa patches prepared in Examples 63 to 65 had no defects such as irritation to the affected parts and foreign body sensation, and protected the affected parts for 3 hours or longer.

Examples 66 to 68

Production of the Oral Mucosa Patch

Each hyaluronic acid described in Table 11 was uniformly dissolved in water to prepare each hyaluronic acid aqueous solution. At this time, a hyaluronic acid concentration in each hyaluronic acid aqueous solution was 10 mg/ml. Subsequently, the resulting hyaluronic acid aqueous solution was put into a plastic petri dish having a base area of 9.1 cm$^2$ so that the hyaluronic acid content per unit area was 7.5 mg/cm$^2$, and frozen in a freezer at −82° C. Then, the hyaluronic acid aqueous solution was lyophilized in the petri dish at a pressure of 10 Pa or lower (24 hours) to obtain a lyophilizate of the hyaluronic acid. The resulting lyophilizate was used as an oral mucosa patch. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 11.

TABLE 11

|  | Types of hyaluronic acid | Property | Stickability | Remaining state |
|---|---|---|---|---|
| Example 66 | Hyaluronic acid (600,000; HA-LQ60) | A | A | B |
| Example 67 | Hyaluronic acid (800,000; HYABEST (J)) | A | A | B |
| Example 68 | Sodium carboxymethyl hyaluronate | A | A | A |

Examples 69 to 72

Production of the Oral Mucosa Patch

The hyaluronic acid (molecular weight: 2,300,000) and each of other polymers (polymer different from hyaluronic acid) described in Table 12 were uniformly dissolved (crystalline cellulose was uniformly dispersed) in water to prepare each aqueous solution so that the hyaluronic acid content was 80 mass % and the other polymer content was 20 mass %. In Example 71, a uniform aqueous solution of the hyaluronic acid and the alginic acid was prepared, then 0.2 part by weight of calcium chloride was added to 1 part by weight of alginic acid, and uniformly dissolved to prepare an aqueous solution for lyophilization. The total concentration of the hyaluronic acid and the other polymer in each aqueous solution was 10 mg/ml. The resulting hyaluronic acid aqueous solution was put into a plastic petri dish having a base area of 9.1 cm² so that the polymer content including the hyaluronic acid per unit area was 7.5 mg/cm², and frozen in a freezer at −82° C. Then, the hyaluronic acid aqueous solution was lyophilized in the petri dish at a pressure of 10 Pa or lower (24 hours) to obtain a lyophilizate. The resulting lyophilizate was used as an oral mucosa patch. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 12.

TABLE 12

|  | Other polymer (content: 20 mass %) | Property | Stickability | Remaining state |
|---|---|---|---|---|
| Example 69 | Agarose | B | A | A |
| Example 70 | Alginic acid | A | A | A |
| Example 71 | Calcium alginate | A | A | A |
| Example 72 | Crystalline cellulose | A | A | A |

Examples 73 to 75

Production of the Oral Mucosa Patch

The hyaluronic acid (molecular weight: 2,300,000) and each of sugars/polyhydric alcohols were uniformly dissolved in water to prepare each aqueous solution so that the hyaluronic acid content and the sugar/polyhydric alcohol content were at the percentages (mass %) described in Table 13. At this time, the hyaluronic acid concentration in each aqueous solution was 10 mg/ml. The resulting hyaluronic acid aqueous solution was put into a plastic petri dish having a base area of 9.1 cm² so that the hyaluronic acid content per unit area was 7.5 mg/cm², and frozen in a freezer at −82° C. Then, the hyaluronic acid aqueous solution was lyophilized in the petri dish at a pressure of 10 Pa or lower (for 24 hours) to obtain a lyophilizate of the sugar/polyhydric alcohol-containing hyaluronic acid. The resulting lyophilizate was used as an oral mucosa patch. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 13. Since the oral mucosa patches in Examples 73 to 75 contained the sugars/polyhydric alcohols in the lyophilizate, the properties of the oral mucosa patches included elasticity, and the handleability was further improved. In addition, the oral mucosa patches (gelled matter) 10 minutes after sticking exhibited high elasticity.

TABLE 13

|  | Contents of hyaluronic acid and sugar/ polyhydric alcohol (mass %) | Property | Stickability | Remaining state |
|---|---|---|---|---|
| Example 73 | Hyaluronic acid; 75% Mannitol; 25% | B | A | A |
| Example 74 | Hyaluronic acid; 50% Mannitol; 50% | B | A | A |
| Example 75 | Hyaluronic acid; 75% Polyethyleneglycol 400; 25% | A | A | A |

Examples 76 to 80

Production of the Oral Mucosa Patch

The hyaluronic acid (molecular weight; 2,300,000) was uniformly dissolved in water to prepare an aqueous solution with a hyaluronic acid concentration of 10 mg/ml. Subsequently, the resulting hyaluronic acid aqueous solution was put into a plastic petri dish having a base area of 9.1 cm² so that the hyaluronic acid content per unit area was 7.5 mg/cm², and frozen in a freezer at −82° C. Subsequently, the other polymer and polyethyleneglycol 1000 were uniformly described in water to prepare an aqueous solution so that the other polymer content and the polyethyleneglycol 1000 content were at the percentages (mass %) described in Table 14. The other polymer concentration in this aqueous solution was 10 mg/ml. This aqueous solution was put on the lyophilized hyaluronic acid aqueous solution so that the other polymer content was 1.0 mg/cm², and frozen in a freezer at −82° C. Then, this frozen aqueous solution was lyophilized in the petri dish at a pressure of 10 Pa or lower (24 hours) to obtain an oral mucosa patch composed of two layers of the lyophilizate base. The thickness of each oral mucosa patch was about 0.85 cm. Subsequently, the property of each oral mucosa patch, the states of sticking to and remaining on the oral mucosa were evaluated in the same manner as in Examples 1 to 6. The results are shown in Table 14. Since the oral mucosa patches in Examples 76 to 80 had a configuration that the hyaluronic acid-containing lyophilizate was laminated on the other polymer layer (base) with low stickability for the oral mucosa, the patch did not adhere to the lyophilizate as the base even with wet hands when sticking the oral mucosa patch to the oral mucosa, and was particularly excellent in applicability for the oral cavity.

TABLE 14

| | Other polymer used as base (mass %) | Property | Stickability | Remaining state |
|---|---|---|---|---|
| Example 76 | Agarose; 100% | B | A | A |
| Example 77 | Methylcellulose; 80% Agarose; 20% | B | A | A |
| Example 78 | Methylcellulose; 80% Cellulose nanofiber; 20% | B | A | A |
| Example 79 | Methylcellulose; 50% Polyethyleneglycol 1000; 50% | B | A | A |
| Example 80 | Agarose; 25% Polyethyleneglycol 1000; 75% | B | A | A |

Examples 81 to 84

Production of the Oral Mucosa Patch

Each of an aqueous solution with a cellulose nanofiber concentration of 10 mg/ml, an aqueous solution with a cellulose nanofiber concentration of 10 mg/ml and a glycerol concentration of 40 mg/ml, an aqueous solution with an agarose concentration of 10 mg/ml, and an aqueous solution with an agarose concentration of 10 mg/ml and a glycerol concentration of 40 mg/ml was prepared, and each aqueous solution was applied on a polyethylene terephthalate film, and dried in a thermostat at 80° C. for 1 hour to obtain a film product (base) having a thickness of about 50 μm. Subsequently, the hyaluronic acid (molecular weight: 2,300,000) was uniformly dissolved in water to prepare an aqueous solution with a hyaluronic acid concentration of 10 mg/ml. Subsequently, the resulting hyaluronic acid aqueous solution was put into a plastic petri dish having a base area of 9.1 cm$^2$ so that the hyaluronic acid content per unit area was 7.5 mg/cm$^2$, then each film product (base containing other polymer and glycerol shown in Table 15) cut with a punch having a diameter of 3.4 cm was put on the hyaluronic acid aqueous solution, and frozen in a freezer at −82° C. Then, the hyaluronic acid aqueous solution was lyophilized in the petri dish at a pressure of 10 Pa or lower (24 hours) to obtain an oral mucosa patch composed of two layers of the lyophilizate/base. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 15. Since the oral mucosa patches in Examples 81 to 84 had a configuration that the hyaluronic acid-containing lyophilizate was laminated on the base with low stickability for the oral mucosa, the patch did not adhere to the lyophilizate as the base even with wet hands when sticking the oral mucosa patch to the oral mucosa, and was particularly excellent in applicability for the oral cavity.

TABLE 15

| | Contents of other polymer used as base and glycerol (mass %) | Property | Stickability | Remaining state |
|---|---|---|---|---|
| Example 81 | Cellulose nanofiber; 100% | B | A | A |
| Example 82 | Cellulose nanofiber; 20% Glycerol 80% | B | A | A |
| Example 83 | Agarose; 100% | B | A | A |
| Example 84 | Agarose; 20% Glycerol 80% | B | A | A |

Examples 85 to 87

Production of the Oral Mucosa Patch

Alginic acid was uniformly dissolved in water to prepare an aqueous solution with an alginic acid concentration of 10 mg/ml, this aqueous solution was applied on a polyethylene terephthalate film and dried in a thermostat at 80° C. for 1 hour to obtain a film product of alginic acid. This film product was immersed in a 0.2% calcium chloride aqueous solution for 1 hour, then thoroughly washed with ion-exchanged water, and further dried in a thermostat at 80° C. for 1 hour to obtain a calcium alginate film having a thickness of about 50 μm. Another calcium alginate film was separately prepared in the same manner, and then a 10% glycerol aqueous solution corresponding to 4 parts by weight of glycerol relative to 1 part by weight of the calcium alginate film was impregnated into the calcium alginate film, which was then dried in a thermostat at 80° C. for 1 hour to obtain a calcium alginate/glycerol film having a thickness of about 50 μm. Subsequently, the hyaluronic acid (molecular weight: 2,300,000) was uniformly dissolved in water to prepare an aqueous solution with a hyaluronic acid concentration of 10 mg/ml. Subsequently, the resulting hyaluronic acid aqueous solution was put into a plastic petri dish having a base area of 9.1 cm$^2$ so that the hyaluronic acid content per unit area was 7.5 mg/cm$^2$, then each film product (base) or polylactic acid film (base) cut with a punch having a diameter of 3.4 cm was put on the hyaluronic acid aqueous solution, and frozen in a freezer at −82° C. Contents of the other polymer and glycerol used in each base are shown in Table 16. Then, the hyaluronic acid aqueous solution was lyophilized in the petri dish at a pressure of 10 Pa or lower (24 hours) to obtain an oral mucosa patch composed of two layers of the lyophilizate/base. The thickness of each oral mucosa patch was about 0.75 cm. Subsequently, the property of each oral mucosa patch, the states of sticking to and remaining on the oral mucosa were evaluated in the same manner as in Examples 1 to 6. The results are shown in Table 16. Since the oral mucosa patches in Examples 85 to 87 had a configuration that the hyaluronic acid-containing lyophilizate was laminated on the base with low stickability for the oral mucosa, the patch did not adhere to the lyophilizate as the base even with wet hands when sticking the oral mucosa patch to the oral mucosa, and was particularly excellent in applicability for the oral cavity.

TABLE 16

|  | Contents of other polymer used as base and glycerol (mass %) | Property | Stickability | Remaining state |
|---|---|---|---|---|
| Example 85 | Calcium alginate; 100% | B | A | A |
| Example 86 | Calcium alginate; 20% Glycerol80% | B | A | A |
| Example 87 | Polylactic acid; 100% | A | A | A |

DESCRIPTION OF REFERENCE SIGNS

1: Lyophilizate
2: Base
10: Oral mucosa patch
10a: Adherend surface with oral mucosa

The invention claimed is:

1. An oral mucosa patch comprising a lyophilizate comprising a polymer, wherein
the lyophilizate comprises at least 20 mass % of the polymer,
the polymer comprises at least 50 mass % of a hyaluronic acid, and
the lyophilizate forms an adhesive surface that adheres the oral mucosa patch to oral mucosa wherein an intrinsic viscosity of the hyaluronic acid is at least 3 dL/g.

2. The oral mucosa patch according to claim 1, wherein the hyaluronic acid has a molecular weight of at least $1 \times 10^5$ daltons.

3. The oral mucosa patch according to claim 1, wherein, the intrinsic viscosity being measured by:
preparing a solution by measuring out 50 mg of hyaluronic acid and dissolving the hyaluronic acid in a 0.2 mol/L sodium chloride solution so that a total volume is 100 mL,
preparing 10 mL, 15 mL and 20 mL samples of the solution and adding the 0.2 mol/L sodium chloride solution to each of the samples so that a total volume in each of the samples is 25 mL,
determining a specific viscosity and a reduced viscosity for each sample and the 0.2 mol/L sodium chloride solution under an environment at 30.0±0.1° C., and according to the following equations:

Specific viscosity=(Number of seconds for the sample to flow÷Number of seconds for the 0.2 mol/L sodium chloride solution to flow)−1, Reduced viscosity=Specific viscosity÷Hyaluronic acid concentration (g/100 mL), and determining the intrinsic viscosity based on the determined specific viscosity and the determined reduced viscosity.

4. The oral mucosa patch according to claim 1, wherein a content of the hyaluronic acid in the lyophilizate is at least 0.1 mg/cm$^2$.

5. The oral mucosa patch according to claim 1, further comprising:
a base;
wherein the lyophilizate is laminated on the base.

6. The oral mucosa patch according to claim 1, wherein the lyophilizate comprises 0 to 20 mass % of a polymer different from the hyaluronic acid.

7. The oral mucosa patch according to claim 1, wherein the lyophilizate further comprises an acid different from the hyaluronic acid.

8. The oral mucosa patch according to claim 1, wherein the lyophilizate further comprises at least one of a sugar and a polyhydric alcohol.

9. The oral mucosa patch according to claim 1, which is effective for preventing or treating an oral mucosal disease.

10. The oral mucosa patch according to claim 9, wherein the oral mucosal disease is caused by cancer treatment.

11. The oral mucosa patch according to claim 1, which is used for hyposensitization therapy applied to the oral mucosa.

12. The oral mucosa patch according to claim 1, which is used for a transoral mucosally-absorbable preparation applied to the oral mucosa.

13. A method for producing the oral mucosa patch according to claim 1, comprising:
preparing an aqueous solution containing a polymer;
lyophilizing the aqueous solution,
wherein, as the polymer, a polymer at least 50 mass % of hyaluronic acid is used.

* * * * *